United States Patent
Fritzsche et al.

(10) Patent No.: US 6,878,539 B1
(45) Date of Patent: Apr. 12, 2005

(54) AFFINITY SENSOR FOR DETECTING SPECIFIC MOLECULAR BINDING EVENTS AND USE THEREOF

(75) Inventors: Wolfgang Fritzsche, Jena (DE); Andrea Czaki, Camburg (DE); Johann Michael Köhler, Golmsdorf (DE); Antje Wiegand, Jena (DE); Louis Oosting, Groningen (NL); Frederik Schut, Groningen (NL); Paris Som Tjwan Tan, Haren (NL)

(73) Assignee: Genetrix B.V., Haren (NL)

( * ) Notice: Subject to any disclaimer, the term of this patent is extended or adjusted under 35 U.S.C. 154(b) by 0 days.

(21) Appl. No.: 09/869,206
(22) PCT Filed: Dec. 22, 1999
(86) PCT No.: PCT/EP99/10334
§ 371 (c)(1), (2), (4) Date: Jun. 25, 2001
(87) PCT Pub. No.: WO00/39325
PCT Pub. Date: Jul. 6, 2000

(30) Foreign Application Priority Data

Dec. 23, 1998 (DE) .......................... 198 60 547

(51) Int. Cl.$^7$ ............................ C12M 1/34; C12M 1/42; C12Q 1/68
(52) U.S. Cl. ............................ 435/287.2; 435/285.2; 435/287.9; 435/288.3; 435/288.7; 435/6; 435/7.1; 436/501; 436/518
(58) Field of Search .................. 435/6, 7.1, 285.2, 435/287.9, 288.3, 288.7, 176; 436/501, 518, 525; 430/512; 324/724

(56) References Cited

U.S. PATENT DOCUMENTS 4,327,073 A  4/1982  Huang
4,794,089 A  12/1988  Mroczkowski et al.

(Continued)

FOREIGN PATENT DOCUMENTS

| DE | 43 18 519 | 12/1994 |
| DE | 195 17789 A | 11/1996 |
| EP | 0 241 771 | 10/1987 |
| WO | WO8808528 | 11/1988 |
| WO | 90/05300 | 5/1990 |
| WO | 97/34140 | 9/1997 |
| WO | WO9741425 A | 11/1997 |

OTHER PUBLICATIONS

Mar. 1, 1990 Electrochemical Behavior of Reversible Redox Species at Interdigitated Array Electrodes with Different Geometries: Consideration of Redox Cycling and Collection Efficiency. Osamu Niwa, et al., Analytical Chemistry, vol. 62, No. 5, pp. 447–452.

(Continued)

*Primary Examiner*—Carla J. Myers
(74) *Attorney, Agent, or Firm*—Jordan and Hamburg LLP

(57) ABSTRACT

The invention relates to an affinity sensor for detecting specific molecular binding events, for use in the field of molecular biology, e.g., in medical diagnostics, especially in biosensor technology or in DNA microarreay tests. The aim of the invention is to provide an affinity sensor of this type for rapidity, sensitively, specifically, economically and routinely detecting the presence of molecules, especially bioactive molecules, and to provide special applications for an affinity sensor of this type. To this end, the affinity sensor consists of a support substrate which is provided with at least two electrodes. The electrodes are situated equidistantly from each other and cover an area on both sides, at least this area being provided for receiving immobilized specific binding partners which are capable of coupling complementary corresponding binding partners directly or with other specific binding molecules. The area is established with a minimum width b, in such a way that at least one complementary corresponding binding partner which is provided with an electroconductive particle can be received in the area in such a way as to guarantee the possibility of a tunnel-type contact junction forming between the particle and the electrodes in each case. The affinity sensor is used for biomonitoring.

19 Claims, 2 Drawing Sheets

U.S. PATENT DOCUMENTS

Figure 1:
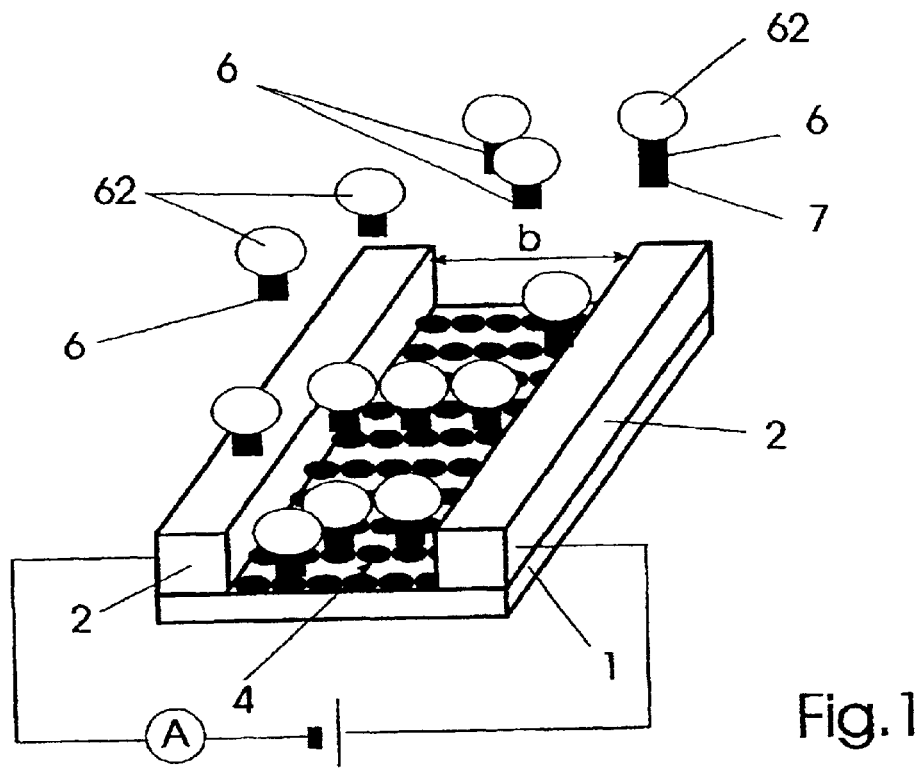

| | | | |
|---|---|---|---|
| 5,077,210 A | | 12/1991 | Eigler et al. ................. 435/176 |
| 5,457,396 A | | 10/1995 | Mori et al. ................. 324/724 |
| 5,494,831 A | | 2/1996 | Kindler ...................... 436/525 |
| 5,552,274 A | * | 9/1996 | Oyama .......................... 435/6 |
| 5,646,420 A | * | 7/1997 | Yamashita ................... 257/17 |
| 5,780,214 A | | 7/1998 | Hagermann et al. ........ 430/512 |
| 6,281,006 B1 | * | 8/2001 | Heller et al. ............. 435/287.9 |
| 6,325,904 B1 | * | 12/2001 | Peeters ....................... 204/403 |

OTHER PUBLICATIONS

DNA–templated assembly and electrode attachment of a conducting silver wire by Erez Braun, Yoav Eichen, Uri Sivan and Gdalyahu Ben–Yoseph, Nature, vol. 391, Feb. 19, 1998, pp. 775–778.

Electrostatic trapping on single conducting nanoparticles between nanoelectrodes, by A. Bezryadin and C. Dekker and G. Schmid, Appl. Phys. Lett. 71 (9), Sep. 1, 1997, pp. 1273–1275.

Accessing Genetic Information with High–Density DNA Arrays, by Mark Chee, et al., Science, vol. 274, Oct. 25, 1996, pp. 610–615.

* cited by examiner

AFFINITY SENSOR FOR DETECTING SPECIFIC MOLECULAR BINDING EVENTS AND USE THEREOF

BACKGROUND OF THE INVENTION

The invention relates to an affinity sensor for detecting specific molecular binding events, as is particularly used in the molecularbiological field, for example, in medical diagnostics, in biosensor technology or in DNA-microarray technology, and application of the same.

Biosensors are solid phase measuring devices that are comprised of at least one biological receptor, a transducer and a subsequently connected electronic unit.

The receptor utilizes biologically active reagents such as, for example, is antibodies for detecting a specific substance such as, for example, antigens. The transduction of detection events into detectable signals is performed by the transducer, for example, by electrochemical, optical, piezoelectric, or calorimetric methods. Thereby, the coupling of the detection events to the transducer can be carried out indirectly or directly. In the first case, the detection events modulate a process which is detected by the transducer. In the second case, the detection events themselves are recorded by the transducer. The transducer is connected to an electronic unit, for example, to a microprocessor followed by modules for signal detection and evaluation.

There are numerous application possibilities for such biosensors operating on the basis of molecular detection. These are, among others, in fields of detection and concentration analysis of biomolecules, kinetic and equilibrium analysis of biochemical reactions, control of fermentation processes, evaluation of receptor-cell-interactions, clinical analysis, and cell demotion.

The detection of the presence of bioactive molecules will be performed in the case of nucleic acids, for example, by hybridization with specific and marked nucleic acid probes. The marking of the probes is achieved by enzymatic inclusion of nucleotides that carry radioisotopes such as, for example, tritium, sulphur-35 or phosphorus-32, non-radioactive molecules such as, for example, digoxigenin or biotin and non-radioactive fluorescent molecules, respectively, such as, for example, fluoresceinisothiocyanat or 7-amino-4methylcumarin-3-acetate or metallic particles such as, for example, gold (Nicholl, D. S. T., 1995: Genetische Methoden, Spektrumis Akademischer Verlag Heidelberg, p. 24–27).

In the case of antigens, such as peptides or proteins, the detection of the presence of bioactive molecules is achieved by specific and marked antibodies. The marking of the antibodies is performed by coupling of radioisotopes such as, for example, iodine-125 or tritium, to tyrosine-residuals and histidine-residuals, respectively, by nonradioactive enzymes, for example, alkaline phosphatase or peroxidase, whereby the enzymatic activity is measured, for example, by the conversion of a colorless product into a colored one, by nonradioactive enzymes, for example, haematin which effects the chemiluminescent reaction of hydrogen peroxide and luminol, by nonradioactive enzymes, for example, luciferase which effects bioluminescence by means of phosphorized luciferin, or by metallic particles such as, for example, gold (Liddell, E. and Weeks, I., 1996: Antikoerpertechniken, Spektrum Akademischer Verlag Heidelberg, p. 87–107).

The signals from the various marker-molecules used will be evaluated by radio-chemical or electrochemical methods, by optical, piezoelectric, or calorimetric methods for indicating molecular detection events. Thereby, the size of the marker-molecules which emit single signals will lie in the nanometer area.

The optical and electrochemical methods for representing molecular binding events are the currently most utilized ones.

The problem of the various optical methods is, that the sensitivity and the spatial resolution of the signals emitted by the individual markermolecules is too low for many applications, that the binding between two links of a specific molecular binding pair cannot be detected, and that the signals are very often superimposed by an unspecific background. These problems of image generating methods can only be eliminated in part by an experimental amplification of the signal or by a computer aided statistical image analyzing method.

The technical limits of the current automation of the image analyzing on the basis of chip technology lies in a read-out of various microarray spots. Most of the available technologies are based on detection of fluorescence marked binding pairs, which are held in a specific manner to a surface of a chip, whereby the fluorescence detection is performed by an optical read-out of reactive centers of microarrays. The application of fluorescent or chemiluminescent samples is thereby utilized just as in the conventional method described hereinbefore and is combined with the CCD-imaging (Eggers, M. et al., 1996: Professional Program Proceedings, in Electro '96. IEEE, New York, N.Y., USA, 364 pp.; Heller, M. J., 1996: IEEE Engineering-in-Medicine-and-Biology-Magazine 15: 100–104), whereby also here the mentioned problems of the conventional image analyzing occur and a binding between two links of a specific molecular binding pair cannot be detected.

The detection of the presence of bioactive molecules can also be obtained by an electrochemical approach by various methods, apart from the commonly used optical methods.

The measurement of redox potency variations in biomolecules is a well-known possibility, which is accompanied by specific binding events, for example, on enzymes. Thereby, the redox potential variations are measured by way of a single electrode, which is provided with molecules, and a reference electrode (Heller, A., 1992: Electrical connection of enzyme redox centers to electrodes, J. Phys. Chem. 96: 3579–3587).

The disadvantage of this method lies in the fact that only one single electronic event occurs for one biomolecular binding event, whereby the variation of the redox state, which is effected, lasts only for a short time, so that the detection of each individual binding event had to take place flash-like. This is not possible. The signal obtained is only cumulative so that rare binding events cannot be detected by this as technology.

A further possibility for detecting the presence of bioactive molecules in an electrical way is to use biosensors in the form of special measuring electrodes. Such special measuring electrodes generally are comprised of a (strepto)-avidin coated electrode, whereby the (strepto)-avidin has the property to specifically bind biotin molecules. In this way it is possible to detect peptides, oligonucleotides, oligosaccharides and polysaccharides as well as lipides which are marked with biotin or biotin-derivatives, respectively to couple these as ligands to the (strepto)-avid-layer. In the latter case, the biotin molecules are the coupling elements. Generally, these biosensors allow detection of antibody/antigen binding pairs, antibody/partial antigen binding pairs, saccharide/lectin binding pairs, protein/nucleic acids binding pairs, and nucleinic acids/nucleinic acids binding pairs. The detection of the biochemical events occurring at the special measuring electrode takes place in a similar way to that of the before described technology based on redox system, namely, by measuring the potential variations across a single electrode compared to a reference electrode (Davis, et al., 1995: Element of biosensor construction; Enzyme Microb. Technol. 17: 130–1035).

A substantial disadvantage of this conventional biosensor technology is the inherent low sensitivity of the measurements at across the measuring electrodes that cannot be eliminated in that the ligands in an infinitely great density are bound to the measuring electrode, for example, by use of a dextran layer. Due to the additional deposition of, as for example, a dextran layer and due to the spatial arrangement of the ligands, the concentration of ligands on the electrodes is indeed raised up to the sixfold compared to a ligand single layer, but a detection of rare binding events or even of a binding between two elements of a special molecular binding pair is not possible.

Further known possibilities are:

the anchoring of specific antibodies on a semiconductor gate of a field-effect transistor, whereby a variation in the charge distribution and, hence, in the circuit of the field-effect transistor is obtained by the selective binding of antigens to the special antibody layer;

the immobilizing of special antibodies on the surface of an fiber, whereby measurable optical phenomena such as, for example, interfering waves and surface plasmons appear due to the selective binding of antigens to special antibody layers at the site of intersection between the fiber optics and the liquid;

as well as the method of surface plasmon resonance, in which, at a definite angle of incidence of light, the refractive index of a medium is, due to the selective coupling of antigens, measurably varied at a metal-coated glass body which is provided with specific antibodies (Liddell E. and Weeks, 1., 1996: Antikoerpertechniken, Spektrum Akademischer Verlag Heidelberg, p. 156–158).

The disadvantage of these methods is that rare binding events cannot be detected by these technologies.

At present there are only a few methods available which allow a rapid detection of bindings between molecules at low concentrations or even with single molecule pairs (Lemieux, Bertrand et al., "Overview of DNA chip technology." Molecular Breading 4: 277–289, 1988), though the biochemical process of the binding pair formation with biosensors, for example, the hybridization of two nucleotide strands or the binding of antibodies to antigens itself runs very quickly, that is, within the area of seconds; biochips can be provided with binding molecules, for example, with specific oligonucleotides (U.S. Pat. No. 5,445,934) or specific proteins (U.S. Pat. No. 5,077,210) so that a chip technology will be possible (Osborne, J. C., 1994: Genosensors. Conference Record of WESCON/94. Idea/Microelectronics. IEEE, New York, N.Y. USA: 434 pp.; Eggers, M. D. et al., 1993: Genosensors, microfabricated devices for automated DNA sequence analysis. Proc. SPIE-Int. Soc. Opt. Eng. 1998), by which the presence of definite biomolecules can be detected within a few minutes, for example, the presence of genes by use of specific oligonucleotide probes or antigens by use of specific antibodies, and by which great prod are indited in the field of biology or medicine, particularly as concerns genetic investigations (Chee, M. et al. 1996: Accessing genetic information with high-density DNA arrays. Science 274: 610–614).

A very promising approach as concerns the detection of binding events between nucleic acid bindings has recently been given by the utilization of the dielectric relaxation frequencies of the DNA to distinguish between hybridized and non-hybridized samples (Beattie et al. 1993. Clin Chem. 39: 719–722). The detection of the differences in frequencies, however, requires equipment which still is very expensive and which, moreover, still is far from being utilized as a matter of routine.

Furthermore, there is known another way to electronically distinguish hybridized samples from non-hybridized ones, which consists in determining the speed of the electron movements along the DNA strands (U.S. Pat. No. 5,780,234). This determination is based on the fact that the arrangement of the pi-electron orbits in the double-ended DNA causes the electrons to move faster in double-stranded DNA, that is, in hybridized DNA than in single-stranded DNA (Lipkin et al., 1995: Identifying DNA by the speed of electrons Science News 147, 117 pp.). To allow for a determination of these electron movements, the target has to be positioned exactly between two molecules. One of these molecules has to be chemically modified in such a way that it acts as an electron donor and the other one such, that it acts as an electron acceptor, so that there is a flow of electrons via electrodes measurable.

This expensive method has the disadvantage that it limits its application to the detection of single-sanded nucleic acids fragments of a defined length and that it is not suited for further biomolecules.

Furthermore, one of the methods for an electrical detection of particles is known from Bezryadin, A., Dekker, C., and Schmid G., 1997: "Electrostatic trapping single conducting nanoparticles between nanoelectrodes." in Applied Physics Leers 71: 1273–1275, in which nanoparticles are captured in a gap formed by electrode in that a voltage is applied across the electrodes and the capturing of the particles is detected by way of the flow of the current. In contrast to the binding events of biomolecule pairs there is no specific biochemical binding of the nanoparticles, but the particle is bound to the electrode gap by the electric field.

There is also known from a work by Braun, E., Eichen, Y., Sivan, U., and Ben-Yoseph, G., 1998: "DNA templated assembly and electrode attachment of a conducting silver wire." in Nature 391: 775–778, that DNA molecules can be held between two micro structurized electrodes and these molecule only exhibited an electric conductivity after having been silver coated, whereby this conductivity has nothing to do with specific biochemical binding events of biomolecule pairs.

Alivisatos, A. P., Johnson, K. P., Peng, X., Wilson, T. E., Loweth, C. J., Bruchez Jr. M., P. and Schulz, P., G., 1996: "Organization of nanocrystal molecules using DNA" in Nature 382: 609–611, generated complexes from short single-stringed DNA-molecules and their complementary single-stringed DNA-molecules marked with gold-particles in solution and deposited these on a TEM-grid with a carbon film for a characterization by electron microscope. An electric characterization, however, of the molecule pair binding did not take place.

SUMMARY OF THE INVENTION

It is an object of the present invention to provide an affinity sensor for detecting specific molecular binding events, which in a rapid, sensitive, specific way detects the presence of molecules in routine operation at low expenditures, in particular the presence of bioactive molecules, as well as to provide for special applications of such an affinity sensor.

According to the invention, the object is realized by the features of the claims. More specifically, an affinity sensor consists of a base on which electrodes are disposed in a spaced apart relation capturing an area that is provided with immobilized specified binding partners,
which specifically couple complimentary associated binding partners, whereby said binding partners carry electrically conductive particles, so that there can be formed an electrically conductive contact between the electrodes and in this way the variation of the electrical
resistance is detectable, when there is a potential applied across the electrodes, as well as the presence of single or a plurality of complementarily at binding partners, carrying electrically conductive particles.

DETAILED DESCRIPTION OF THE INVENTION

Figure 2:
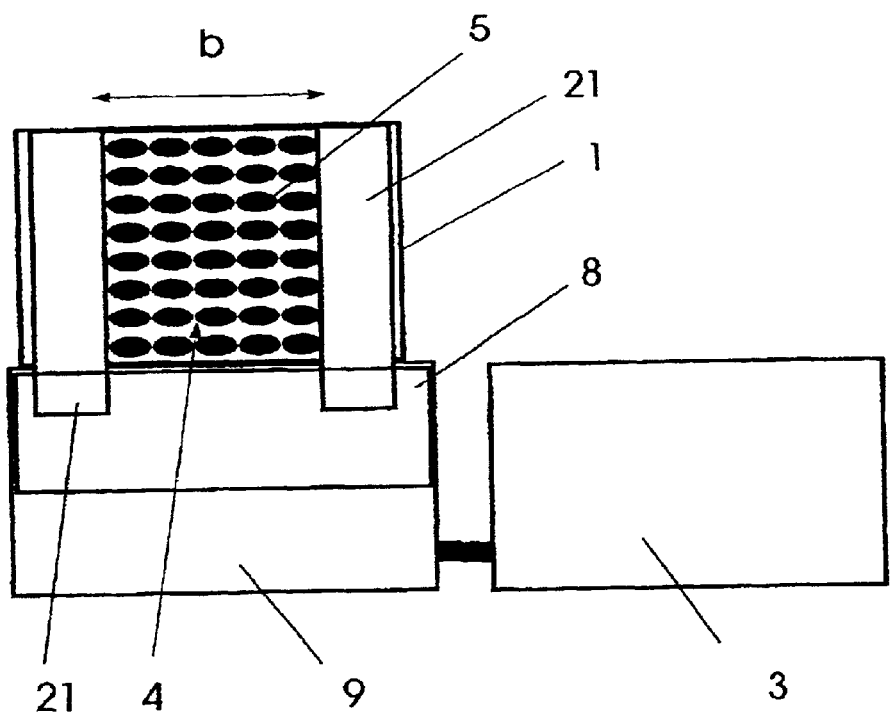
Figure 3:
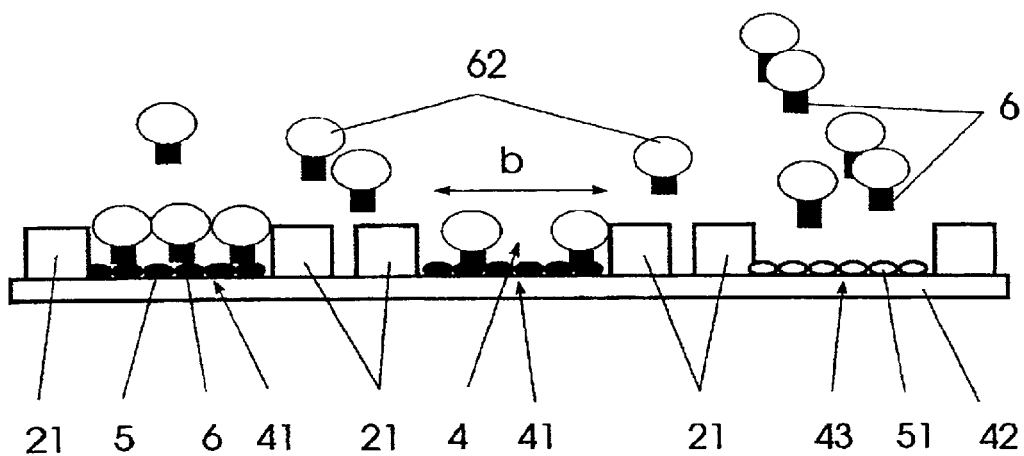
Figure 4:
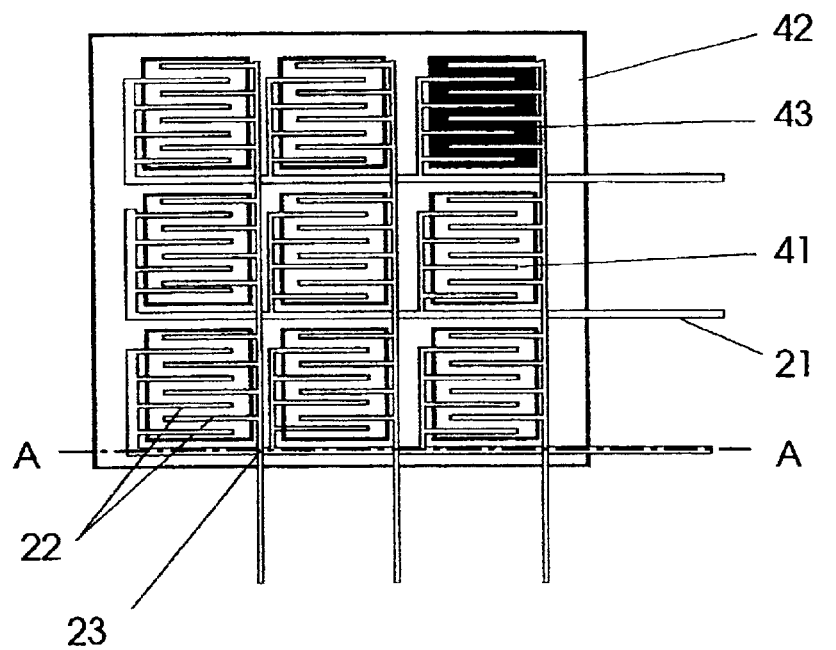
Figure 5:
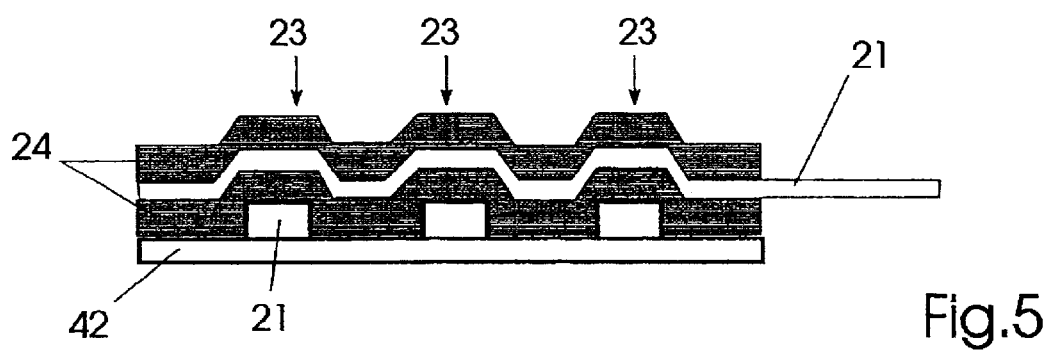

The invention will be explained hereinafter in more detail by virtue of schematical embodiments under reference to the drawings. There is shown in:

FIG. 1 an affinity sensor for detecting specific molecular binding events,

FIG. 2 a schematical representation of the affinity sensor for detecting specific molecular binding events, FIG. 3 a cross-sectional view of an embodiment of the affinity sensor for detecting specific molecular binding events, FIG. 4 a plan view of an embodiment of the affinity sensor in the form of an affinity chip, and FIG. 5 a sectional view along the plane A—A of the affinity chip represented in FIG. 4.

DETAILED DESCRIPTION

An affinity sensor for detecting specific molecular binding events shown in FIGS. 1 and 2, is comprised of a carrier subsonic 1 which is provided with electrodes 2 enclosing an area 4 ta is provided with immobilized specific binding partners 5. Thereby the area 4 represents a discontinuity in an electric circuit that includes an amplifier circuit 8, which can be part of a microchip 9, as well as a measuring and evaluating unit 3, whereby in the present example the electrodes 2, which limit the area 4, are connected to the electric circuit and define a minimum width b of the area 4. The specific binding partners 5 are cape of coupling complementarily associated binding partners 6 specifically and directly or via further specific is binding molecules 7, whereby the complementarily associated binding partners 6 including electrically conductive particles 62 are directly coupled or coupled via binding molecules. The area 4 is, by the arrangement of the electrodes 2, so dimensioned in its width and effective height to detect the coupling of the immobilized specific binding partners 5 to the complementarily associated binding partner 6 which carry the electrically conductive particles 62 or, via further specific binding molecules 7, with the complementarily associated binding partners 6 which carry the electrically conductive particles 62. Provided that the specific binding partners 5 are realized by molecules of a nucleic acid probe species, the complementarily associated binding partners 6, which carry the electrically conductive particles 62, by nucleic acids and the electrically conductive particles 62 by nanoparticles of a size of 20 nm, then the minimum width b of the area 4 is 25 nm and its effective height 20 mm.

The coupling of the specific binding partners 5 in the area 4 to the complementarily associated binding partners 6 carrying the electrically conductive particles 62 effects, when there is applied a voltage across the electrodes 2 (refer to FIG. 1), the motion of the electrons via an electron transport barrier in such a way that the electrically conductive particles 62 bridge the area 4 so that electrons tunnel from particle 62 to particle 62 and to the electrodes 2, as a result thereof a permanent variation of the electric resistance across the area 4 between the electrodes 2 can be measured by aid of the post-connected amplifier circuit 8 in combination with the measuring and evaluating unit 3.

The measurements can also be performed in a humid environment, in particular by aid of a gel layer, instead of measuring in a dry state.

In order to enhance the electric conductivity of the area 4 between the electrodes 2, which is achieved by way of the complementarily associated binding partners 6 in cooperation with the electrically conductive particles 62, already known electron-transfer-mediators or effective diffusing electron donors and electron acceptors can be used, such as water soluble ferrocene/ferricinium, reducible and oxidizable components from organic salts, cobaltocenes, hexacyanides and octacyanides of molybdenum, tungsten, and iron, respectively, macrocycles and chelating ligands from the transition metals such as cobalt, ruthenium, and nickel, including Co(ethylenediamine)3- and Ru(ethylenediamine)3- and trisbipyridyland hexamine-complexes from transition metals such as Co, Ru, Fe, and/respectively, organic molecules such as 4-4'-bipyridines and 4mercaptopyridines, which are free in solution or present in a gel deposited on the carrier substrate 1 or in a polymer deposited on the carrier substrate 1. When a known gel-based matrix immobilization utilizes nucleic acids as specific binding partners 5 then, due to a three-dimensional structure of the polymer, it exhibits an advantage that a greater number of capturing ligands are immobilized on the small surface section of the area 4. By using a highly porous hydro-gel, the hybridization rate, for example, of the nucleic acids which are the specific binding partners S and the complementarily associated binding partners 6, which carry the electrically conductive particles 62, is increased and lies within areas as they are known for nucleic acids in solution.

The affinity sensor shown in FIGS. 3 and 4, which is in the form of a affinity chip, is characterized in that the electrodes 2 are designed as micro-electrodes 21, which are arranged in two p each, capturing a respective affinity area 41. Thus, a matrix of affinity areas 41 results, which is adapted to simultaneously and electrically detect in the different interspaces 4 a plurality of various couplings.

Thereby, the individual affinity areas 41 are designed in an interdigital electrode structure arranged upon a chip surface 42. The chip surface 42 consists of silicon or glass upon which, for example, a dielectric oxide layer is provided. Due to the digitally branched microelectrodes 21, which, for example, can be manufactured to yield the shape of comb-like electrodes 22, the areas 4 on the affinity area 41 can be defined to have a length within a area of 20 $\mu$m. The microelectrodes 21 are spaced apart and electrically separated from each other by an inter insulating layer 24, as shown in FIG. 5, which is provided at the intersections 23 of the micro-electrodes 21. Thereby and provided that the specific binding partners 5 are realized by the molecules of a nucleic acid probe species, the complementarily associated binding partners 6, which carry the electrically conductive particles 62, are nucleic acids and the electrically conductive particles 62 are nanoparticles of a size of 20 nm, then the areas 4 have an effective height of 100 nm and a width of 200 nm. Consequently, at least one coupling, which establishes a contact between the microelectrodes 21, is achieved between the immobilized specific binding partners 5 and the complementarily associated binding partners 6 which carry the electrically conductive particles 62. In this example, the immobilized specific binding partners 5 are capturing ligands in the form of nucleic acid probes and the complementarily associated binding partners 6, which carry the electrically conductive particles 62, are target molecules in the form of nucleic acids. The oligonucleotide probes immobilized as specific binding partners 5 are bound to a silanized carrier substrate 1 via an amino group, whereby a probe density in an order of size of 10,000 molecules per U M2 is attained in this example. The complementarily associated binding partners are oligonucleotides in this example, which are marked with as gold particles, the hybridization conditions depending on the respectively used probes.

Alternatively, the affinity areas 41 can be provided with various immobilized specific binding partners 5 in sirs, which are respectively separated from each other.

Affinity areas 41 with immobilized specific binding partners 5 and reference areas 43 with immobilized inactive binding partners 51 are provided on affinity chips, represented in FIGS. 3 and 4, so that the measurement of the electric resistance between the micro-electrodes 21 is carried out as a reference measurement of the electric resistance between an affinity area 41 and a reference area 43, whereby the micro-electrodes 21 can be designed as comb-type electrodes 22. Thereby the immobilized specific binding partners 5 and the immobilized inactive binding partners 51 can be of a thickness which, when covering the electrodes 21, permits the tunnel effect, rendering the manufacture of the chips technologically more easier.

Since the reference area 43 is free from immobilized specific binding partners 5, due to the occupation by inactive binding partners 51, this space between the two microelectrodes 21, insulated from each other, represents an electrical barrier so that there does not take place a measurable electron transfer between them.

The affinity area 41, which in con thereto carries immobilized specific binding partners 5, binds via the latter and through the coupling event the complementarily associated electrical binding partners 6, which carry the electrically conductive particles 62, so that as a result—hereof, by the conducive particles 62, conduction occurs. The space of the affinity areas 41 between the micro-electrodes 21, which are designed as comb-type electrodes 22, is divided into a plurality of gaps of nanometer width. The nano-gap formed by the electrically conductive particles 62 result in that an electron transfer is possible between the two contact faces of the micro-electrodes 21 by virtue of the tunnel effect, so that the variation of the resistance can be detected via the amplifier circuit 8 by means of a measuring and evaluating uni 3, when there is a voltage applied across the micro-electrodes 21. In the present example, the voltage applied lies in an order of size of less than one volt.

Alternatively to the measurement of the potential applied across the affinity area 41 by an electrode system comprised of reference electrode, sample electrode and counter electrode, it is also possible to employ other methods of an electrical detection such as, for example, potentiometric and voltametric measurements.

Standard chemical linker such as, for example, aminomodified ligands, are used to immobilize the specific binding partners 5 and the inactive binding partners 51, respectively, such as, for example, antibodies or nucleotide probe so that the chemical linkers are bound to the silanized chip surface 42 and constitute the affinity areas 41 and the reference areas 43, respectively.

The marking of the complementarily associated binding partners 6 such as, for example, protein targets or the target nucleic acid, by means of electrically conductive particles 62 is performed according to the known methods such as, for example, the final marking with marked oligonucleotides, by utilizing ligases.

In the following, the manufacturing of affinity sensors according to the present will be described in more detail. In a preferred embodiment the affinity sensor is comprised of a plurality of areas 4 (also referred to as detection areas), whereby each of which is captured by at least two electrodes 2. These detection areas are provided with specific binding partners (capture molecules) 5 such as antibodies, fragments of antibodies or DNA-, RNA- or PNA-oligonucleotides, to which definite associated binding partners (target molecules) 6 bind in a specific manner. The specific binding partners 5 are defined as marked or non-marked molecules, which can be selected for being bound to the desired target molecule in the areas 4 of the affinity sensor. To this end, not only conventional (bio)molecular binding pairs can be utilized as capturing molecules and as target molecules, but also specifical chemical binding pairs as known from combinatorial is chemistry, which can also be utilized as binding pairs within the frame of the invention. The formation of this described specific binding can be understood as a primary binding event. It is possible to carry out the detection of this primary binding in a one-step procedure or in a multi-step procedure, whereby the specific co-immobilization of the material, which transfers the electrons, for example, the gold particles 62, is carried out in the last step each. This co-immobilization can be performed by specific kinds or unspecific kinds of molecular interaction, such as a hybridization of probes marked with gold onto the desired-target molecule or by a direct marking of the target molecule with the properties of an electron transfer in such a way that this marking can be electronically detected. The mentioned coimmobilization is, in principle, separated from the primary binding event, in dependence, however, therefrom and can be performed simultaneously. Thus, the co-immobilization or attachment of material, which transfers electrons, to the designated surface of the affinity sensors can be taken as an indirect result of the primary binding. The detection of this co-immobilization is obtained by an electronic measurement of the variation of the electric conductivity across the measuring area, this variation of the electric conductivity being an indication of the presence of target molecules. The primary binding of electron-transferring material can be exploited to induce secondary depositions which are adapted to transport electrons. It lies within the scope of the present invention that the specific binding of target molecules can be detected by way of a multi-step process, which comprises at least one step by way of which electron-transferring material is deposited, this material effecting a reduction of the electric resistance across the measuring area. It is possible to use organic or inorganic substances or compounds for the electron conductive particles 62. This conductivity, is used for detecting and marking of the desired target molecule, that is, for detecting the presence thereof.

In the following and without limiting the present invention thereto there will be described several possibilities of preparation steps for manufacturing an affinity sensor according to the pro invention.

A. To prepare the required electrodes, a silicon wafer having on one side an oxide layer of about 1 µm thickness is coated by sputtering with a bonding layer, for example, of 3 nm Ti, to the oxide layer and a gold layer of a thickness of 50–10 nn. To be able to provide for the electron gap width in the lower nanometer area, a multi-layer masking is utilized for the micro-structuring. To this end, a coating with a carbon (30 nm) is performed, followed by a coating with a metal combination (Ti and NiCr, respectively, of a thickness of 10 nm). Subsequently, an electron bean resist (150 nm) is deposited by spinning-on. The exposure is realized by a mix-technology, in the course of which the large-area electrodes 2 are generated by means of a shaped-electron-bean exposure device and the minute gaps between the electrodes 2 by means of a point-beam electron-beam exposure device. The structure is transferred to the metal layer by ionbeam etching (IBE) and to the carbon layer by a reactive ion-etching (RIE). The transfer of the structure to the gold-layer and the bonding layer is carried out by way of an IBE-process. Finally, the masking layer is removed in an O2 RE-process at a simultaneous surface activation.

In the following, techniques will be described which are based on a silanization of the surface of the chips. Due to this silanization, the surfaces are activated for binding amino-modified oligonucleotides. Two different methods for the silanization and subsequent immobilization will be explained here. Of course, there are also other possibilities for surface activation and immobilization, apart from the silanization.

B.1. Silanization by Application of 3-aminopropyltrimethoxysilane APTES:

The pre-structured chips with gold electrodes, as described by example under A., are purged in an ultrasonic bath and, in sequence in concentrated nitric acid, in hydrogen peroxide solution (30%) and water, and subsequently dried for 5 minutes at 80° C. Then the chips will be incubi for 2 min. in a 1% silane solution in 95% acetone/water. After having been washed for ten times in acetone for 5 minutes each, the chips will be dried at 110° C. Then they will be incubated for 2 h in a 0.2%-phenylenediisothiocyanate solution in 10% pyridine/dimethylformamide and washed with methanol and acetone. Chips activated in this manner can be stored in a desiccator at 4° C. for a longer time.

Subsequently, the linkage of the amino-modified oligonucleotides is performed, to this purpose a drop of the oligonucleotide solution (2 mM in 100 mM sodium carbonate/sodium bicarbonate buffer) is deposited upon the chip. The parallel application of small drops of different oligonucleotides allows a parallelization, for example, by use of an embodiment of the affinity sensor according to FIG. 4. The deposition of the mentioned drops call be performed by means of micro-pipettes, spotters or other available techniques suited for the application of small amounts of samples. Then, the chips are incubated in a moisture chamber at 37° C. for about 1–2 h. After removal of the drops the—chips will be washed with 1%—ammonia solution for one time, and three-times with water. Then drying is carried out at ambient temperature.

B.2. A second possibility of silanization is carried out by application of 3-glycidoxypropyltrimethoxysilane (GOPS), to this end, as described under B 1., the chips are purged and subsequently are treated in an ultrasonic bath, each for 12 min. with hexane, acetone and ethanol. Then the chips are dried for 5 minutes at 80° C. The silanization is carried out with 1 mM GOPS in dry toluol at 80*C for 6–8 h. The chips are thoroughly washed with ethyl acetate and are ready for immediate use.

Subsequently, the linkage of the amino-modified oligonucleotides performed. To this purpose a drop of the oligonucleotide solution (550 µM in 0.1M KOH) is deposited upon the chip and the chip is incubated in the moisture chamber at 37° C. for 6 h. Again a parallelization, as referred to under B.1. can be obtained due to the deposition of a plurality of drops with different oligonucleotides. Then the drops are allowed to dry, and then washing is carried out with water at 50° C. under continuous shaking, followed by drying at ambient temperature.

C. In this part of the specification there will be described the possibility of marking oligonucleotide probes with colloidal gold. To start with, there is required a preparation of the thiolated oligonucleotide, which is carried out as follows: the 3'-alkylthiol modified oligonucleotides are solid-phase bound to a dithiolcompound lay the manufacturer to protect its functional group. By separation from the carrier material the functional group will be released and is then in the active state. The separation takes place in 50 mM DTT (dithiothreitol) in concentrated ammonium hydroxide at 55° C. for 16 h (original solution: 4–8 mg solid-phase bound oligonucleotide, 450 µl water, 50 µl 1M DTT, 50 µl cc ammonium hydroxide). After incubation the liquid phase is separated from the solid phase (Controlled Pored Glass, CPG) and desalinated by way of column chromatography. The oligonucleotides are then washed out in reaction buffers. The concentration of the single chromatography fractions is then detected by spectrophotometer.

The reaction solution will be incubated at 55° C. for 16 h at 600 revolutions per minute in a thermomixer, and then centrifugated for 2–3 min. at an acceleration of about 16,000 m/s$^2$. Fractions that are prepared in this manner can be stored for more than 4 weeks at −20° C. The binding of the thiolated oligonucleotides to colloidal gold will be described by example in the following:

There are added to 5 ml gold solution (about 17 nM) 2.5 OD (260 nm) alkylthiololigonucleotides, (final concentration 3.6 nM). Subsequently to a pre-incubation for 16 h at ambient Thereafter, again a centrifugation takes place for 25 min. at an acceleration of about 16,000 m/s$^2$. Fractions that are prepared in this manner can be stored for more than 4 weeks at −20° C. The binding of the thiolated oligonucleotides to colloidal gold will be described by example in the following:

There are added to 5 ml gold solution (about 17 nM) 2.5 OD (260 nm) alkylthiololigonucleotides, (final concentration 3.6 nM). Subsequently to a pre-incubation for 16 h at ambient temperature, incubation is carried out after a setting to 0.1 M NaCl/10 mM sodium phosphate buffer (pH 7.0) for 40 h at ambient temperature. Thereafter, again a centrifugation takes place for 25 min. at an acceleration of about 16,000 m/s$^2$. The resulting pellet is washed with 5 ml 0.1M NaCl/10 mM sodium phosphate buffer (pH 7.0), followed by a further centrifugation for 25 min. at an acceleration of 16,000 m/s$^2$. The re-dispersion is carried out in 5 ml 0.3 M NaCl/10 mM sodium phosphate buffer (pH 7.0). 40 µl of the aqueous solution with colloidal gold particles (diameter of 30 nm in the example) obtained in the above described manner are placed in the area 4 between the electrodes 2. After drying, electric measurements, which have been described herein further up, show a linear current-voltage characteristic which is indicative of an ohmic behaviour of the aggregated gold colloids in the area under consideration. A current of 0.3 μA was measured at a voltage of about 0.3 volt applied across the electrodes 2.

The affinity sensor as, for example, disclosed in connection with FIGS. 3 and 4 and in form of the affinity chips, can find a variety of applications as, for example, in the molecular biology and in the medical diagnostics where specific bindings of bioactive molecules to their corresponding binding partners, for example, DNA, proteins, is saccharides are to be determined.

Based on the electrical detection of specific molecular binding events, the affinity sensor allows to perform a bio-monitoring of, for example, molecules, viruses, bacteria, and cells in the most diverse samples, for example, in clinical samples, in samples of food and from the environment such as, for example, from clarification plants, whereby such monitoring is performed in a quick, sensitive and specific way.

What is claimed is:

1. Affinity sensor for detecting specific binding events in response to a sample medium, comprising:
    a carrier substrate provided with at least two electrodes and having a predetermined area therebetween, said electrodes being equidistantly spaced apart from each other and engagingly bordering said area on opposing sides, at least said area having immobilized specific binding partners for affinity binding complementarily associated binding partners wherein the specific binding partners are nucleic acids; and
    said area being accessible to said complementarily associated binding partners provided in the sample medium and having a minimum width adapted for capture of at least one of said complementarily associated binding partners provided with an electrically conductive particle within said area by affinity binding with said immobilized specific binding partners.

2. Affinity sensor for detecting specific binding events as claimed in claim 1, wherein said width is under 800 nm.

3. Affinity sensor for detecting specific binding events as claimed in claim 1, wherein the immobilized specific binding partners cover said area with a thickness which permits tunnel effects.

4. Affinity sensor for detecting specific binding events as claimed in claim 1, wherein the electrodes are each two micro-electrodes arranged in a pair, the electrodes being connected to an amplifier circuit with an associated measuring and evaluating unit so that an electric current flow across the area can be detected when there is a voltage applied across the electrodes.

5. Affinity sensor for detecting specific binding events as claimed in claim 4, wherein the electrodes are part of the amplifier circuit and project from out of the latter.

6. Affinity sensor for detecting specific binding events as claimed in claim 5, wherein the amplifier circuit is a component of a microchip.

7. Affinity sensor for detecting specific binding events as claimed in claim 1, wherein the electrodes are comb-like structures opposingly meshed, and said predetermined area includes affinity areas positioned between the comb-like structures.

8. Affinity sensor for detecting specific binding events as claimed in claim 7, wherein the comb-like electrodes and the affinity areas are arranged on a common chip surface.

9. Affinity sensor for detecting specific binding events as claimed in claim 8, wherein the chip surface is silicon.

10. Affinity sensor for detecting specific binding events as claimed in claim 8, wherein the chip surface is glass.

11. Affinity sensor for detecting specific binding events as claimed in claim 7, wherein the electrodes are arranged in geometrical symmetry to interdigital structures and said affinity areas are arranged in a matrix, the electrodes are separated from each other at intersections by an insulating layer arranged between the electrodes.

12. Affinity sensor for detecting specific binding events as claimed in claim 7, wherein said electrodes are micro-electrodes and the micro-electrodes have a length of 0.1 mm, the width of the area is 0.1 μm and its effective height is 0.02 μm as well as the affinity areas is at a 1:10 ratio relative to the chip surface.

13. Affinity sensor for detecting specific binding events as in claim 7, wherein in addition to the affinity areas at least one reference area has immobolized inactive binding partners.

14. Affinity sensor for detecting specific binding events as claimed in claim 7, wherein a number of specific binding partners per unit area on the individual affinity areas are different.

15. Affinity sensor for detecting specific binding events as claimed in claim 7, wherein the affinity areas carry different specific binding partners.

16. Affinity sensor for detecting specific binding events as claimed in claim 1, 13, 14 or 15, further comprising a plurality of reference areas having different inactive binding partners.

17. Affinity sensor for detecting specific binding events as claimed in claim 1, wherein the specific binding partners are suited for entering into chemical coordination.

18. Affinity sensor for detecting specific binding events as claimed in claim 1, wherein the conductive particles are of sizes in the range of 0.1 μm to 5 μm.

19. Affinity sensor for detecting specific binding events as claimed in claim 1, wherein the conductive particles consist of metal-cluster compounds.

* * * * *